United States Patent
Nahon et al.

(10) Patent No.: US 9,937,332 B2
(45) Date of Patent: Apr. 10, 2018

(54) CRYO-PERFUSION BALLOON DEVICE

(75) Inventors: Daniel Nahon, Ottawa (CA); Willard W. Hennemann, Hudson (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 2171 days.

(21) Appl. No.: 11/347,854

(22) Filed: Feb. 6, 2006

(65) Prior Publication Data

US 2007/0185445 A1   Aug. 9, 2007

(51) Int. Cl.
  *A61M 25/10*  (2013.01)
  *A61B 18/00*  (2006.01)
  *A61B 18/02*  (2006.01)

(52) U.S. Cl.
  CPC ...... *A61M 25/104* (2013.01); *A61M 25/1011* (2013.01); *A61B 2018/0022* (2013.01); *A61B 2018/0212* (2013.01); *A61B 2018/0262* (2013.01); *A61M 2025/1095* (2013.01); *A61M 2025/1097* (2013.01); *A61M 2202/03* (2013.01)

(58) Field of Classification Search
  CPC ............ A61M 25/1011; A61M 25/104; A61M 2025/1095; A61M 2025/1097
  USPC ................... 604/101.05, 113; 606/21–22, 26
  See application file for complete search history.

(56) References Cited

U.S. PATENT DOCUMENTS

| | | | |
|---|---|---|---|
| 4,423,725 A * | 1/1984 | Baran et al. ............. | 128/207.15 |
| 4,610,662 A * | 9/1986 | Weikl et al. .................. | 604/509 |
| 4,771,177 A | 9/1988 | Horzewski et al. | |
| 4,909,252 A | 3/1990 | Goldberger | |
| 5,090,958 A | 2/1992 | Sahota | |
| 5,100,388 A * | 3/1992 | Behl et al. ..................... | 604/113 |
| 5,160,321 A | 11/1992 | Sahota | |
| 5,199,951 A | 4/1993 | Spears | |
| 5,222,938 A * | 6/1993 | Behl ............................ | 604/500 |
| 5,226,888 A * | 7/1993 | Arney ...................... | 604/103.07 |
| 5,370,617 A * | 12/1994 | Sahota ..................... | 604/102.02 |
| 5,417,653 A * | 5/1995 | Sahota et al. ................... | 604/20 |
| 5,458,574 A * | 10/1995 | Machold et al. ........ | 604/101.03 |
| 5,868,735 A * | 2/1999 | Lafontaine ..................... | 606/21 |
| 5,885,238 A | 3/1999 | Stevens et al. | |
| 6,099,454 A | 8/2000 | Hastings et al. | |
| 6,117,065 A | 9/2000 | Hastings et al. | |
| 6,126,684 A | 10/2000 | Gobin et al. | |
| 6,129,705 A | 10/2000 | Grantz | |
| 6,436,087 B1 | 8/2002 | Lewis et al. | |
| 6,475,187 B1 * | 11/2002 | Gerberding ............. | 604/102.02 |

(Continued)

*Primary Examiner* — Ryan J Severson

(74) *Attorney, Agent, or Firm* — Christopher & Weisberg P.A.

(57) ABSTRACT

The present invention provides a method and apparatus for treating a vascular occlusion and preventing or reducing ischemic consequences of such an obstruction. The medical device of the present invention may include an elongate body defining a proximal end and a distal end, where the elongate body may also define an injection lumen, an exhaust lumen, and a guidewire lumen. A first expandable element may be coupled to the elongate body, where the first expandable element is in fluid communication with the injection lumen and the exhaust lumen. Further, a perfusion path may be disposed within the elongate body, and a sheath may be movably disposed about at least a portion of the elongate body. The medical device may further include a second expandable element disposed about the elongate body, as well as second inflation and exhaust lumens.

4 Claims, 5 Drawing Sheets

(56) References Cited

U.S. PATENT DOCUMENTS

| | | | |
|---|---|---|---|
| 6,576,000 B2 | 6/2003 | Carrison | |
| 6,585,689 B1* | 7/2003 | Macoviak et al. | 604/103.07 |
| 6,622,367 B1* | 9/2003 | Bolduc et al. | 29/447 |
| 6,699,231 B1* | 3/2004 | Sterman et al. | 604/509 |
| 6,719,724 B1* | 4/2004 | Walker et al. | 604/113 |
| 6,726,653 B2* | 4/2004 | Noda et al. | 604/113 |
| 2001/0032004 A1 | 10/2001 | Werneth | |
| 2001/0049495 A1* | 12/2001 | Schwartz | 604/113 |
| 2002/0032430 A1 | 3/2002 | Luo et al. | |
| 2002/0161351 A1* | 10/2002 | Samson et al. | 604/507 |
| 2002/0183692 A1* | 12/2002 | Callister | 604/113 |
| 2003/0036728 A1* | 2/2003 | Samson et al. | 604/103.01 |
| 2003/0187428 A1* | 10/2003 | Lane et al. | 606/21 |
| 2004/0039430 A1* | 2/2004 | Gonzales | 607/105 |

\* cited by examiner

CRYO-PERFUSION BALLOON DEVICE

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to medical devices, more particularly, to a perfusion device for treating ischemia and vascular occlusions.

BACKGROUND OF THE INVENTION

Substantial restriction of blood flow in the vascular system can lead to oxygen deprivation in the affected tissue, which is commonly referred to as ischemia. Ischemia can rapidly cause cellular and neurological necrosis, leading to organ dysfunction and even death. Moreover, ischemic conditions can arise due to vascular occlusions, typically caused by blood clots and/or undesired tissue growth or lesions on the inner walls of blood vessels that reduce blood flow.

It has long been known that reducing tissue temperature, i.e., instituting a hypothermic state, reduces the metabolic rate and thereby provides some protective measure against ischemic consequences. Such hypothermic conditions are routinely induced during invasive surgeries to protect organs such as the brain and heart from surgical interruptions in blood flow. Hypothermia has also been shown to be effective in controlling swelling of the brain in trauma and stroke patients.

In addition to inducing hypothermic conditions during invasive surgery, systemic hypothermia has also been applied, such as by cooling blood going to a specific organ or immersion of the patient's body in a cool bath, where the depth and duration of hypothermia is limited by the patient's ability to tolerate the therapy. While such methods may effectively reduce the temperature and metabolic rate of large portions of a patient's body, such invasive and systemic techniques are excessive and undesirable where ischemic conditions are prevalent in a specific region of the patient's anatomy.

As such, in light of the above limitations, it would be desirable to provide for the treatment of a vascular occlusion while limiting ischemic damage by cooling the tissue affected by the loss of blood flow due to the vascular occlusion.

SUMMARY OF THE INVENTION

The present invention advantageously provides a method and system for treating a vascular occlusion and preventing or reducing ischemic consequences of such an obstruction. The medical device of the present invention may include an elongate body defining a proximal end and a distal end, where the elongate body may also define an injection lumen, an exhaust lumen, and a guidewire lumen. A first expandable element may be coupled to the elongate body, where the first expandable element is in fluid communication with the injection lumen and the exhaust lumen. Further, a perfusion path may be disposed within the elongate body, where the perfusion path may include a perfusion lumen in fluid communication with the guidewire lumen. Moreover, a fluid control element may be movably disposed about at least a portion of the elongate body to selectively limit or otherwise control fluid flow through the perfusion path. The medical device may further include a second expandable element disposed about the elongate body, as well as second inflation and exhaust lumens.

In an exemplary method of use of the medical device of the present invention, the medical device may be positioned in proximity to a vascular occlusion, followed by the expansion of the expandable element with a coolant. As such, the expandable element may thermally affect tissue surrounding the expandable element, while the coolant may further thermally affect at least a portion of the perfusion path. The fluid control element may subsequently be actuated or otherwise engaged to deliver cooled fluid through the perfusion path and downstream of the occlusion.

DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
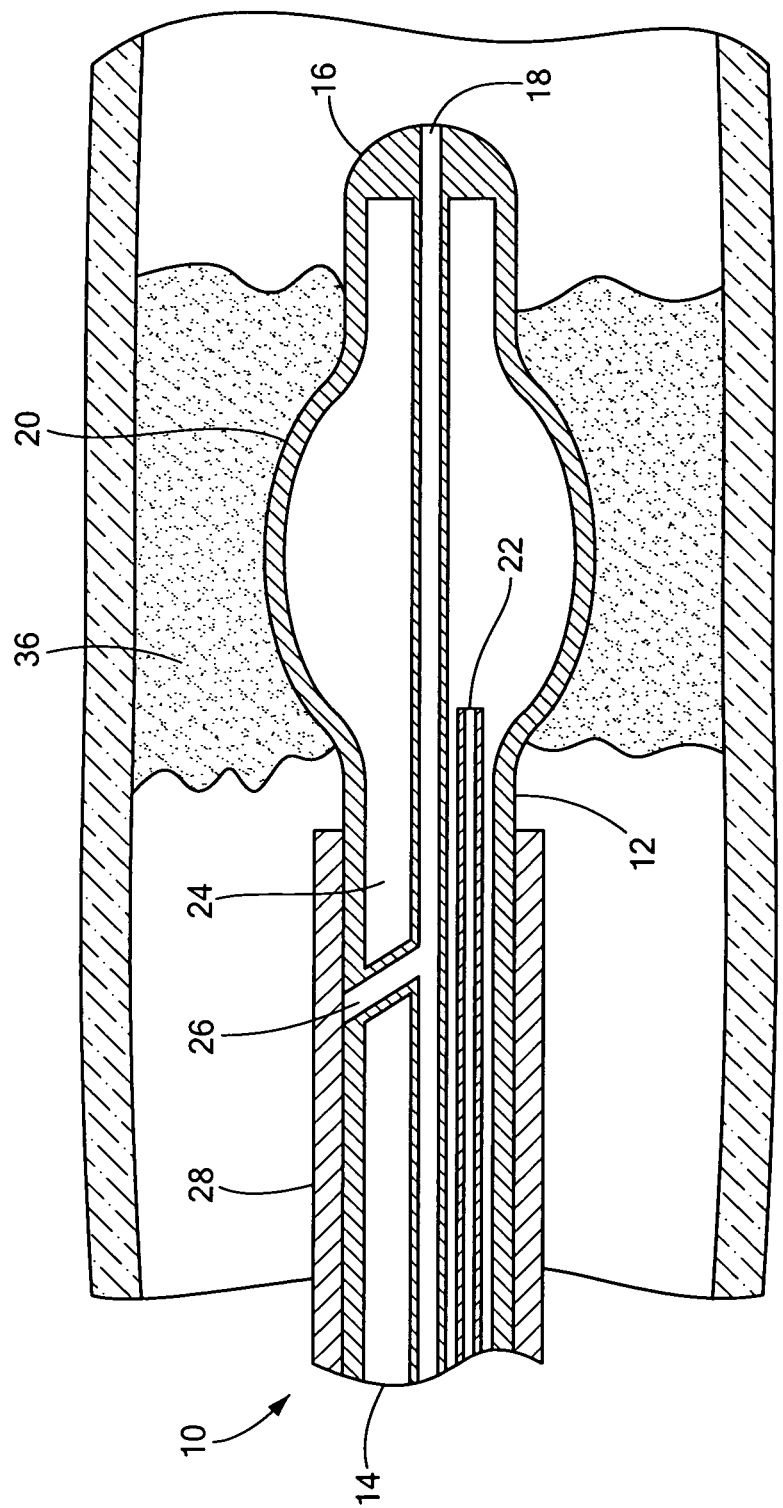
FIG. 1 is a cross-sectional illustration of an embodiment of a medical device in accordance with the present invention.
Figure 2:
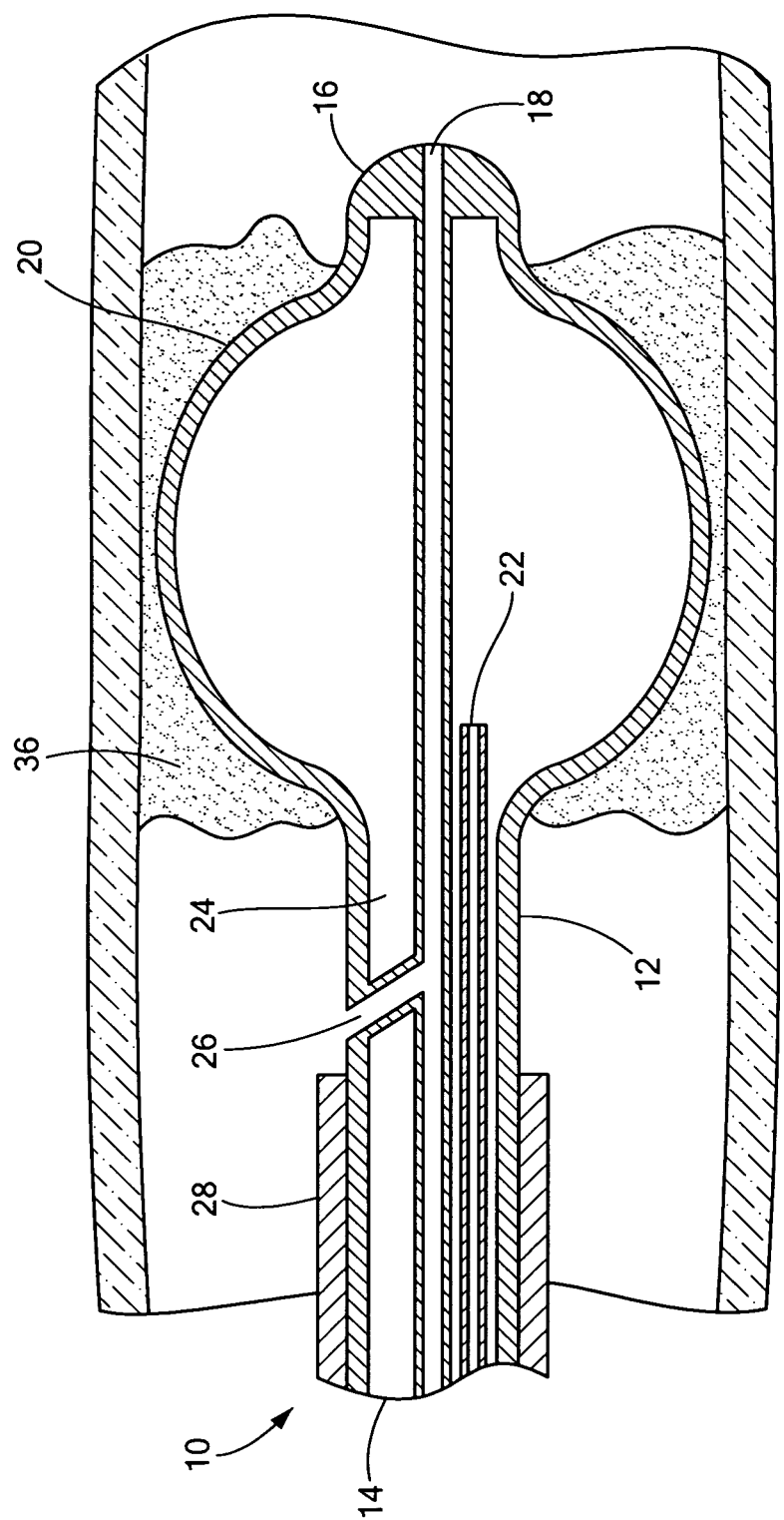
FIG. 2 is an additional cross-sectional illustration of an embodiment of a medical device in accordance with the present invention.

Now referring to FIGS. 1 and 2, the present invention provides a medical device 10 having an elongate body 12 having a proximal end 14 and a distal end 16, where the elongate body 12 defines a guidewire lumen 18 extending through a substantial length of the device. The medical device 10 further includes a first expandable element 20 disposed on or otherwise coupled to the elongate body 12 at a distal region of the device. The first expandable element 20 can include varying shapes, including, for example, substantially rounded or cylindrical shapes, as well as taking the form of a hectically-shaped balloon. Through the use of a hectically-shaped balloon, a hectically-shaped fluid path is formed on the exterior of the medical device 10 between the hectically-shaped balloon and a surface which the balloon may be in contact with.

An inflation lumen 22 is further included, where the inflation lumen 22 is disposed within the elongate body 12 and is in fluid communication with the first expandable element 20. Moreover, the medical device 10 can include an exhaust lumen 24 disposed within the elongate body 12 which is also in fluid communication with the first expandable element 20. The inflation and exhaust lumen 24s may be oriented in various configurations to achieve fluid communication with the first expandable element 20 while maintaining desired operational characteristics of the device, including uniform fluid dispersion, thermal gradients, fluid flow, or device flexibility. For example, the inflation and exhaust lumen 24s may be coaxial with one another, as well as coaxial with the guidewire lumen 18. Alternatively, the lumens may be adjacent to one another along a portion of the length of the catheter, or the inflation lumen 22 may be coiled about a portion of either the guidewire lumen 18 or the exhaust lumen 24, or both.

The medical device 10 of the present invention can further include a perfusion path, i.e., a path able to direct fluid from a proximal region of the first expandable element 20 to a region distal to the first expandable element 20. The perfusion path may include a perfusion lumen 26 disposed within a portion of the elongate body 12, where the perfusion lumen 26 may be in fluid communication with the exterior environment of the medical device 10 at both the proximal and distal portions of the perfusion lumen 26, and may include one or more openings in the elongate body 12 for fluid communication. The perfusion lumen 26 may be positioned proximally to the first expandable element 20, where the perfusion lumen 26 is in fluid communication with the exterior environment of the elongate body 12, and further in fluid communication with the guidewire lumen 18, thereby creating a fluid path traveling through a portion of the device. Additionally, the perfusion lumen 26 may extend from a region proximal of the first expandable element 20 to a region distally of the first expandable element 20.

A fluid control element may also be included with the medical device 10 of the present invention in order to selectively control or otherwise manipulate fluid flow through the perfusion path. For example, the fluid control element may include a guiding catheter or sheath 28 disposed about the elongate body 12 of the medical device 10, such that the sheath 28 is movably positionable along a length of the elongate body 12 where the perfusion lumen 26 is in fluid communication with the exterior environment. As a result, the sheath 28 can be positioned to obstruct the perfusion lumen 26 opening in the region proximal to the first expandable element 20, thereby preventing fluid from entering the perfusion lumen 26. Subsequently, through the use of pull wires or other actuating elements (not shown), or by simply sliding the sheath 28 and/or the elongate body 12 with respect to each other, the sheath 28 can be positioned such that it does not obstruct the perfusion lumen 26, allowing fluid to enter and flow through the perfusion lumen 26 to a distal region of the medical device 10.

Figure 3:
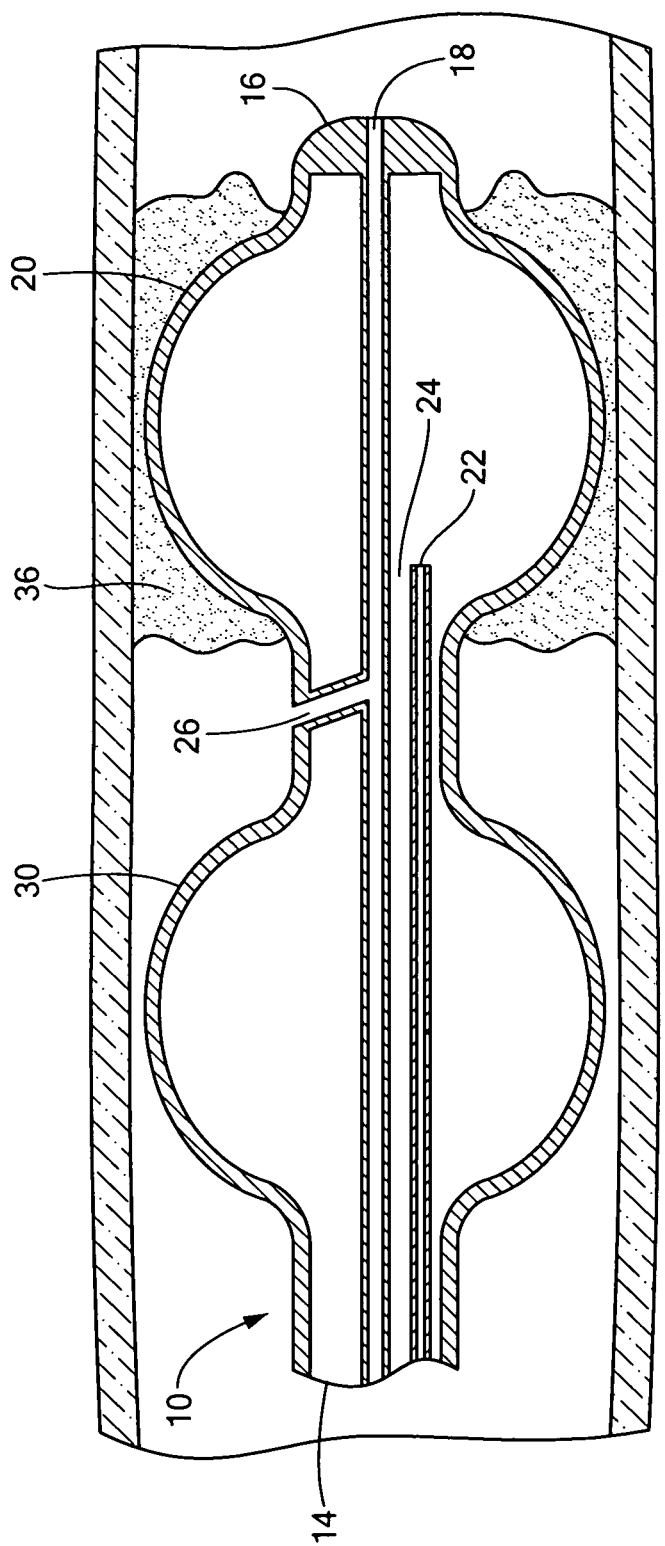
FIG. 3 is yet another cross-sectional illustration of an embodiment of a medical device in accordance with the present invention.
Figure 4:
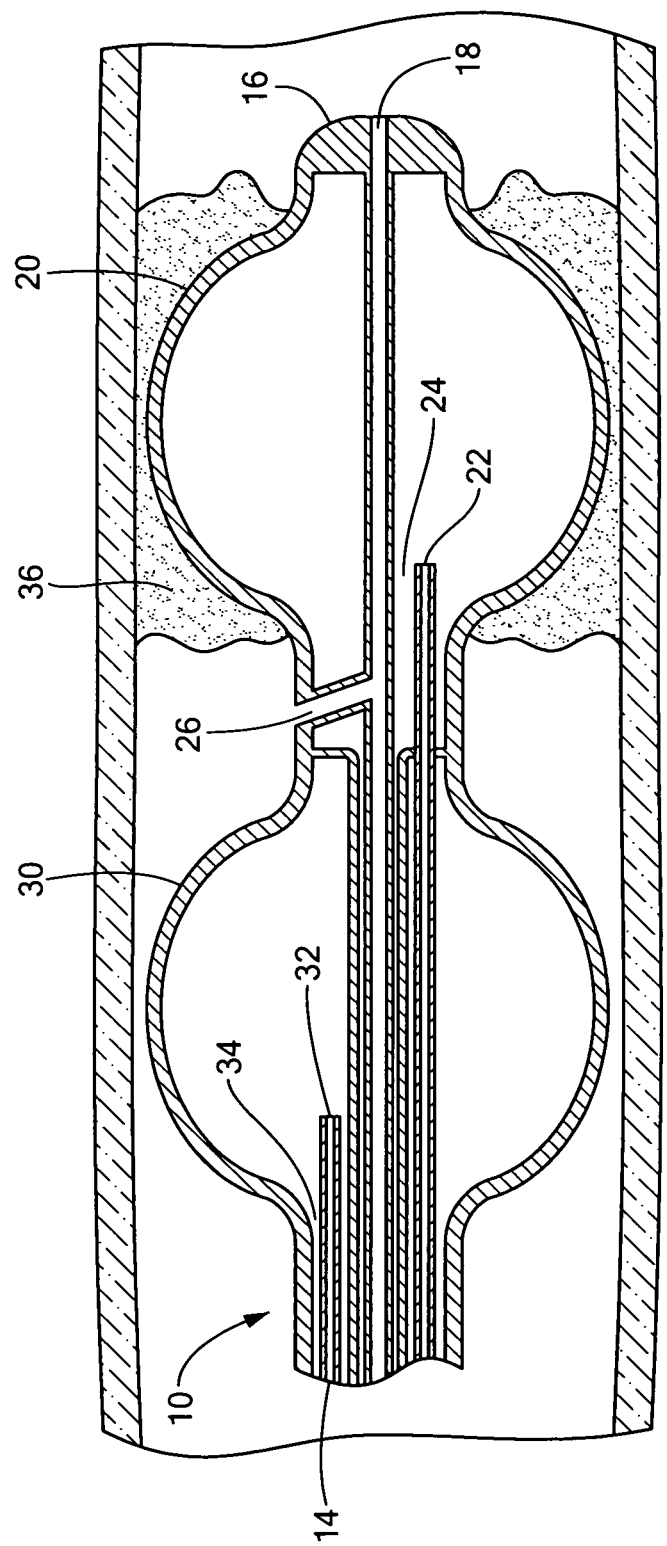
FIG. 4 is a further cross-sectional illustration of an embodiment of a medical device in accordance with the present invention.
Figure 5:
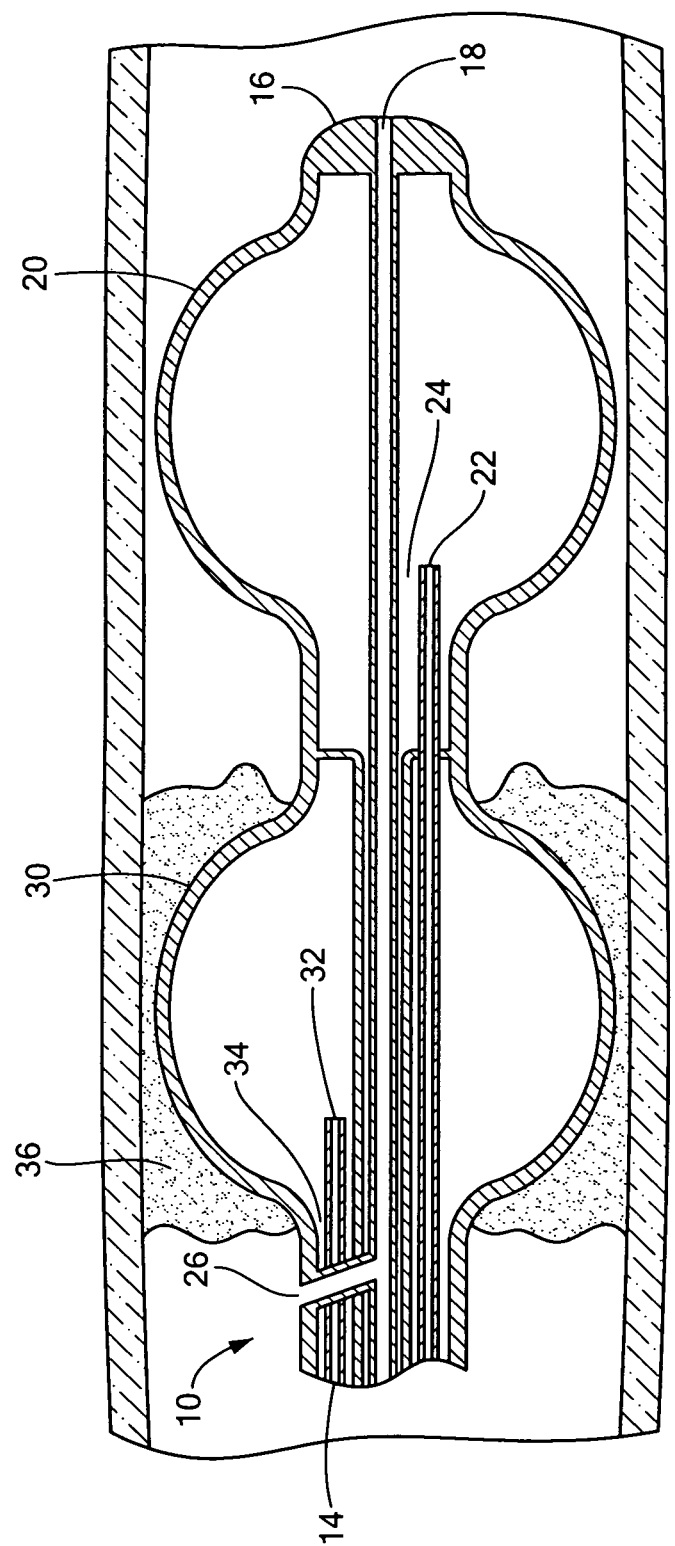
FIG. 5 is still another cross-sectional illustration of an embodiment of a medical device in accordance with the present invention.

Now referring to FIGS. 3 through 5, the medical device 10 of the present invention can further include a second expandable element 30 disposed about the elongate member proximally to the first expandable member. The second expandable element 30 may be in fluid communication with the inflation and exhaust lumens described above, or, alternatively, may be in fluid communication with a second inflation lumen 32 and a second exhaust lumen 34, thereby isolating the expansion and operation of the second expandable element 30 from the operation of the first expandable element 20. Moreover, the perfusion lumen 26 may be positioned either proximally or distally of the second expandable element as to provide additional options and uses for the medical device 10, as described below.

Again referring to FIGS. 1 and 2, in an exemplary use, the medical device 10 of the present invention can be used to treat occlusions or other vascular conditions causing ischemic damage in various tissue regions. The portion of the medical device 10 having the first expandable element 20 can be positioned near a tissue region to be treated, which may include a vascular occlusion 36. Once in the desired location, a coolant can be injected into the inflation lumen 22 for delivery into the first expandable element 20, thereby inflating the first expandable element 20 as well as reducing the temperature of the first expandable element 20 and a portion of the perfusion path. As the first expandable element 20 is inflated, an outer surface of the expandable element will contact the obstruction 36 and/or a surface of the vessel wall. Subsequently, the coolant can be continuously circulated through the inflation lumen 22, first expandable element 20, and the exhaust lumen 24, thereby reducing the temperature of the medical device 10 and directly cooling tissue in contact with the expandable element 20 as well as thermally affecting tissue in the surrounding area. Moreover, while the inflation of the expandable element 20 provides a mechanical force to dilate or otherwise expand the occluded area, the perfusion path may be activated, for example, by manipulating the sheath 28 to allow fluid to flow into the perfusion lumen 26 and towards the region distally of the obstruction 36. Alternatively, in the absence of a sheath or other fluid control element and where the perfusion path includes the guidewire lumen, a guidewire may be either extended or retracted within the guidewire lumen to manipulate the fluid flowing through the perfusion path. As the guidewire may significantly obstruct the perfusion path due to the generally minimal clearance between the outer diameter of the guidewire and the inner diameter of the guidewire lumen, an alternative means of controlling fluid flow through the medical device is thereby provided. As the blood flows through the cooled portion of perfusion path of the medical device 10, the temperature of the blood will be reduced, thereby reducing the temperature of tissue exposed to the blood at the region distal to the medical device 10 and the obstruction 36, resulting in a reduction of ischemic consequences in the affected tissue.

Now referring to FIGS. 3 and 4, in an exemplary use of the medical device 10 including the second expandable element 30, the medical device 10 may be positioned such that the first expandable element 20 is in proximity to a vascular occlusion 36. Upon achieving the desired position, the second expandable element 30 may be expanded to contact a surface of the affected vessel, thereby occluding the region of the vessel proximal to the vascular occlusion 36 and preventing blood from entering the perfusion lumen 26. Subsequently, the first expandable element 20 may be expanded through the introduction of a coolant, which will reduce the temperature of the distal portion of the medical device 10 as well as the vascular occlusion 36 and the tissue surrounding the obstruction 36, while at the same time dilating the vessel and/or the vascular occlusion 36. Once the desired temperature has been reached, the second expandable element 30 may be retracted or otherwise deflated, thereby allowing fluid to flow into the perfusion lumen 26, a portion of which is also thermally affected by the introduction of the coolant into the first expandable element 20. As a result, as previously described, the temperature of the blood will be reduced, thereby reducing the temperature of tissue exposed to the blood at the region distal to the medical device 10 and the occlusion, resulting in a reduction of ischemic consequences in the affected tissue.

Now referring to FIG. 5, in an alternative method of use of the medical device 10 including the second expandable element 30, the medical device 10 may be positioned such that the second expandable element 30 is in proximity to the vascular occlusion 36, while the first expandable element 20 passes through the vascular occlusion 36 to a position distal of the vascular occlusion 36. Subsequently, the first expandable element 20 may be expanded through the introduction of a coolant, which will reduce the temperature of the distal portion of the medical device 10 as well as the tissue distal to or downstream of the vascular occlusion 36. Furthermore, the second expandable element 30 may be expanded to dilate the vessel and/or the vascular occlusion 36. Should the medical device include separate inflation and exhaust lumens for the first and second expandable elements, the dilation of the vascular occlusion 36 by the second expandable element 30 may be performed separate from and independently of the cooling induced by the first expandable element 20. As such, the duration at which dilation is performed and the duration at which cooling is induced may be independently controlled, allowing for variations in the lengths of time that the two stages are performed, i.e., cooling may require a longer duration of expansion of the first expandable element 20, while dilation may require a shorter duration of expansion of the second expandable element 30, or vice versa.

Once the desired dilation and/or cooling has been achieved, the perfusion path, which may be located proximally of the second expandable element, may be opened to fluid flow, either through manipulation of the sheath or by movement of the guidewire as discussed above, thereby allowing fluid to flow into the perfusion lumen 26. As a portion of the perfusion path is thermally affected by the introduction of the coolant into the first expandable element 20, the temperature of the blood flowing through the perfusion path will be reduced, thereby reducing the temperature of tissue exposed to the blood at the region distal to the medical device 10 and the occlusion, resulting in a reduction of ischemic consequences in the affected tissue.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongate body defining a proximal end and a distal end, the elongate body further defining an inflation lumen defining a fluid pathway longitudinally extended through the elongate body and an exhaust lumen defining a fluid pathway longitudinally extended through the elongate body adjacent to the inflation lumen;
   a first expandable element coupled to the elongate body, wherein the first expandable element is in fluid communication with the inflation lumen and the exhaust lumen;
   a second expandable element coupled to the elongate body at a location proximal of the first expandable element, wherein the second expandable element is in fluid communication with the inflation lumen and the exhaust lumen; and
   a perfusion path disposed within the elongate body through an interior of the first expandable element and an interior of the second expandable element, the perfusion path being thermally affected by the first expandable element and including a perfusion lumen defining an inlet aperture in the elongate body at a location between the first expandable element and the second expandable element that is in fluid communication with an environment external to the device, at least a portion of the perfusion path extending from the perfusion lumen to a region distal of the first expandable element and defining an outlet aperture that is in fluid communication with the environment external to the device and in fluid communication with the inlet aperture, wherein the second expandable element controls a fluid flow rate into the inlet aperture of the perfusion lumen.

2. The medical device according to claim 1, wherein the perfusion path includes a guidewire lumen.

3. The medical device according to claim 2, wherein the perfusion lumen is in fluid communication with the guidewire lumen.

4. The medical device according to claim 1, wherein the first expandable element surrounds at least a portion of the perfusion path.

* * * * *